(12) United States Patent
Harvey et al.

(10) Patent No.: US 7,959,611 B2
(45) Date of Patent: Jun. 14, 2011

(54) URINARY CATHETER IMMOBILIZER

(76) Inventors: Dan Harvey, Redding, CA (US); Chris Harris, Redding, CA (US)

( * ) Notice: Subject to any disclaimer, the term of this patent is extended or adjusted under 35 U.S.C. 154(b) by 72 days.

(21) Appl. No.: 12/402,670

(22) Filed: Mar. 12, 2009

(65) Prior Publication Data

US 2009/0234294 A1 Sep. 17, 2009

Related U.S. Application Data

(60) Provisional application No. 61/035,799, filed on Mar. 12, 2008.

(51) Int. Cl.
*A61M 25/02* (2006.01)
(52) U.S. Cl. ....................................... 604/174
(58) Field of Classification Search ................... 604/174, 604/101, 171, 544
See application file for complete search history.

(56) References Cited

U.S. PATENT DOCUMENTS

| | | | |
|---|---|---|---|
| 4,378,018 A * | 3/1983 | Alexander et al. | 604/350 |
| 4,419,097 A | 12/1983 | Rowland | |
| 4,615,692 A * | 10/1986 | Giacalone et al. | 604/94.01 |
| 4,710,169 A * | 12/1987 | Christopher | 604/104 |
| 4,810,247 A | 3/1989 | Glassman | |
| 5,318,551 A * | 6/1994 | Di Cristo | 604/349 |
| 5,593,389 A | 1/1997 | Chang | |
| 5,795,334 A | 8/1998 | Cochrane, III | |
| 2001/0005782 A1 | 6/2001 | Tanghoj et al. | |
| 2007/0088280 A1 | 4/2007 | Gomez | |

* cited by examiner

*Primary Examiner* — Kevin C Sirmons
*Assistant Examiner* — Michael J Anderson
(74) *Attorney, Agent, or Firm* — Jay Schloff

(57) ABSTRACT

Disclosed is a urinary catheter immobilizer for immobilizing movement of a urinary catheter in a human body. The urinary catheter immobilizer comprises a funnel-shaped member and a body member configured to be received over the funnel-shaped member. The funnel-shaped member has a first end portion and a second end portion. The first end portion is capable of being received over a urinary meatus of the human body. The body member is configured to be received over the second end portion of the funnel-shaped member and capable of removably attaching to an external portion of the urinary catheter. The body member comprises a torus-shaped structure and at least one elongated tubular structure. The torus-shaped structure comprises at least one channel. The at least one channel is capable of receiving the at least one elongated tubular structure for looping around the torus-shaped structure for immobilizing the urinary catheter.

6 Claims, 6 Drawing Sheets

URINARY CATHETER IMMOBILIZER

CROSS REFERENCE TO RELATED APPLICATIONS

The present invention claims priority under 35 United States Code, Section 119 on the provisional application No. 61/035,799 filed on Mar. 12, 2008, the disclosure of which is incorporated by reference.

FIELD OF THE INVENTION

The present invention generally relates to bodily mounted fluidic connection systems, and, more particularly, to a urinary catheter immobilizer capable of immobilizing movement of a bodily mounted fluidic connection system such as a urinary catheter, in a human body.

BACKGROUND OF THE INVENTION

The human excretory system functions to remove wastes such as carbon dioxide, water, salt, urea and uric acid from a human body. Ammonia is a nitrogenous waste formed from the breakdown of protein within the human body and is a highly toxic chemical. Ammonia is converted to urea and uric acid by liver and transported to kidneys for excretion purposes. The kidneys pass the urea and the uric acid out of the human body in form of urine. The urine is a watery solution of waste products, organic compounds, urea and uric acid.

Sometimes, the human body fails to excrete urine which may pose a life threatening problem. Inability of the human body to excrete urine may be due to various reasons, which include but are not limited to, a blockage to the flow of the urine, an inability of a urinary bladder to perform regular excretory functions, effect of an accident on the excretory system, and effect of a medical procedure on the human excretory system. The inability of the urinary bladder to empty the urine therein can result in a buildup of urine, which may induce backpressure in the kidneys and in turn may result in kidney failure.

Medical science has made several attempts to address the problem relating to the inability of the human body to voluntarily pass urine out of the body. One such attempt is a bodily mounted fluidic connection system that helps to drain the urine out of the human body. One of the most widely used fluidic connection systems is a urinary catheter. Typically, the urinary catheter is a hollow, flexible tube used to drain the urine from the urinary bladder. Generally, the urinary catheter is inserted into urinary tract through urinary meatus of a patient. An end portion of the urinary catheter extending outside the human body is attached to a bag for collection of urine. The urine is drained from the urinary bladder by the aid of the urinary catheter and is collected in the bag. However, the urinary catheter may be subject to movement within the urinary tract due to various reasons, such as movement of the wearer or the weight of the bag attached to the urinary catheter. The movement of the urinary catheter within the urinary tract may lead to medical complications which includes but are not limited to, urinary tract infections, and damage to the urethra or bladder. Further, medical research has shown that the urinary tract infections are the largest single group of healthcare associated infections.

To address the above, attempts have been made to immobilize the urinary catheter in the urinary tract. The most common practice for reducing movement of the urinary catheter in the body of a patient includes attachment of the portion of the urinary catheter that extends outside the body, to a leg portion of the patient with the help of a securement device or tape. However, the attempts to secure and immobilize the urinary catheter within the urinary tract have not been successful with respect to anchoring the urinary catheter because of the increased likelihood of the urinary catheter slipping from the securement device or the tape.

Accordingly, there exists a need for immobilizing movement of a bodily mounted fluidic connection system such as a urinary catheter, in a human body.

SUMMARY OF THE INVENTION

In view of the foregoing disadvantages inherent in the prior art, the general purpose of the present invention is to provide a urinary catheter immobilizer for immobilizing movement of a urinary catheter in a human body, to include all advantages of the prior art, and to overcome the drawbacks inherent in the prior art.

An object of the present invention is to provide a urinary catheter immobilizer for preventing movement of a urinary catheter within a urinary tract of a human body to prevent urinary tract infections.

Another object of the present invention is to provide a urinary catheter immobilizer which is lightweight, reliable, safe, user friendly, and having low production cost.

To achieve the above objects, in an aspect of the present invention, a urinary catheter immobilizer for immobilizing movement of a urinary catheter in a human body is provided. The urinary catheter immobilizer comprises a funnel-shaped member and a body member configured to be received over the funnel-shaped member. The funnel-shaped member has a first end portion and a second end portion. The first end portion is capable of being received over a urinary meatus of the human body. The body member is capable of removably attaching to an external portion of the urinary catheter proximate to the urinary meatus of the human body. The body member comprises a torus-shaped structure having an inner circumferential surface and an outer circumferential surface. The inner circumferential surface configures a cavity for receiving the external portion of the urinary catheter and the outer circumferential surface comprises at least one channel. Further, the body member comprises at least one elongated tubular structure extending from the outer circumferential surface of the torus-shaped structure. The at least one elongated tubular structure is adapted to be received in the at least one channel for looping around the torus-shaped structure to secure the body member onto the external portion of the urinary catheter.

Further, in another aspect of the present invention, a urinary catheter immobilizer for immobilizing movement of a urinary catheter in a female human body is provided, the urinary catheter immobilizer comprises an adapter pad, a funnel-shaped member and a body member. The adapter pad is configured to be received over a urinary meatus of the female human body. The funnel-shaped member has a first end portion and a second end portion. The first end portion is configured to be received over the adapter pad. The body member is configured to be received over the second end portion of the funnel-shaped member. Further, the body member is capable of removably attaching to an external portion of the urinary catheter proximate to the urinary meatus of the female human body. The body member comprises a torus-shaped structure and at least one elongated tubular structure. The torus-shaped structure has an inner circumferential surface and an outer circumferential surface. The inner circumferential surface configures a cavity for receiving the external portion of the urinary catheter and the outer circumferential surface comprises at least one channel. The at least one elongated tubular structure extends from the outer circumferential surface of the torus-shaped structure. Further, the at least one elongated tubular structure is adapted to be received in the at least one channel for looping around the torus-shaped structure for securing the body member onto the external portion of the urinary catheter.

These together with the other aspects of the present invention, along with the various features of novelty that characterized the present invention, are pointed out with particularity in the claims annexed hereto and form a part of the present invention. For a better understanding of the present invention, its operating advantages, and the specified object attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which:

Like reference numerals refer to like parts throughout the description of several views of the drawings.

DETAILED DESCRIPTION OF THE INVENTION

For a thorough understanding of the present invention, reference is to be made to the following detailed description, including the appended claims, in connection with the above-described drawings. Although the present invention is described in connection with exemplary embodiments, the present invention is not intended to be limited to the specific forms set forth herein. It is understood that various omissions and substitutions of equivalents are contemplated as circumstances may suggest or render expedient, but these are intended to cover the application or implementation without departing from the spirit or scope of the claims of the present invention. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The terms, "first," "second," and the like, herein do not denote any order, elevation or importance, but rather are used to distinguish placement of one element over another. Further, the terms, "a" and "an" herein do not denote a limitation of quantity, but rather denote the presence of at least one of the referenced item.

The term "urinary meatus" used herein, includes both male urinary meatus and female urinary meatus.

The present invention provides a urinary catheter immobilizer for immobilizing movement of a urinary catheter in a human body. The present invention is capable of restricting movement of urinary catheter, in both male patients and female patients. The present invention finds utility in hospitals, clinics and other health-care institutions and environments. It is envisioned that the present invention may be easily incorporated into a multitude of catheterization processes which include but are not limited to, indwelling catheterization, and intermittent catheterization.

Figure 1:
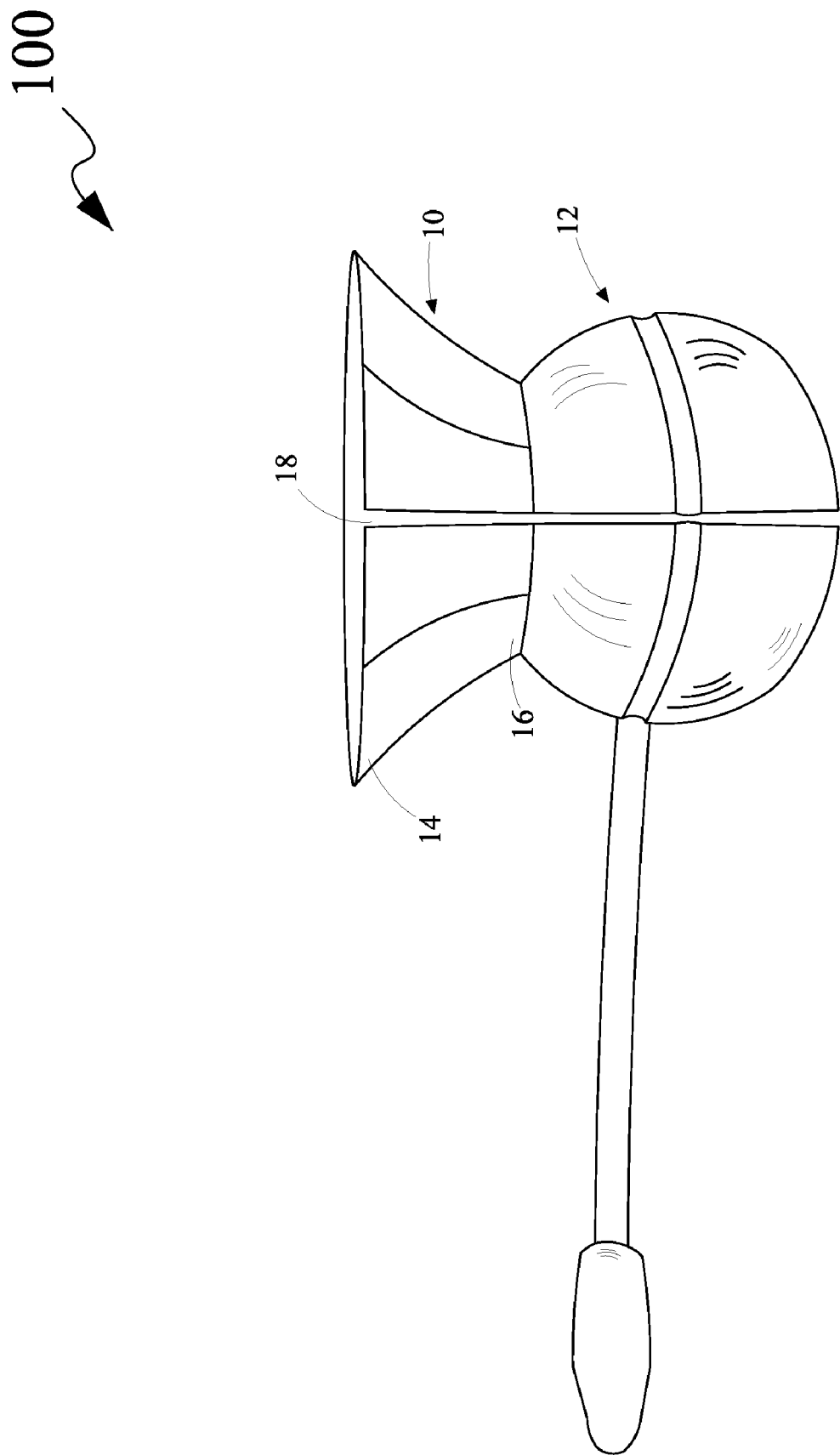
FIG. 1 illustrates a perspective view of a urinary catheter immobilizer, in accordance with an embodiment of the present invention.

Referring now to FIG. 1, a urinary catheter immobilizer 100 for securing a urinary catheter is illustrated, according to an exemplary embodiment of the present invention. The urinary catheter immobilizer 100, as shown in FIG. 1, comprises a funnel-shaped member 10 and a body member 12 capable of removably attaching with the funnel-shaped member 10. Further, the funnel-shaped member 10 is configured to be received over a urinary meatus of a patient. The funnel-shaped member 10 and the body member 12 are elastic and flexible in order to receive and removably secure the urinary catheter. The funnel-shaped member 10 includes a first end portion 14 and a second end portion 16. The second end portion 16 is smaller in diameter than the first end portion 14. The body member 12 is capable of being received over the second end portion 16 of the funnel-shaped member 10. Further, an oblong slit 18 extends throughout the length of the funnel-shaped member 10, from the first end portion 14 to the second end portion 16. The structural configuration of the body member 12 has been explained in detail in conjunction with FIG. 2.

Figure 2:
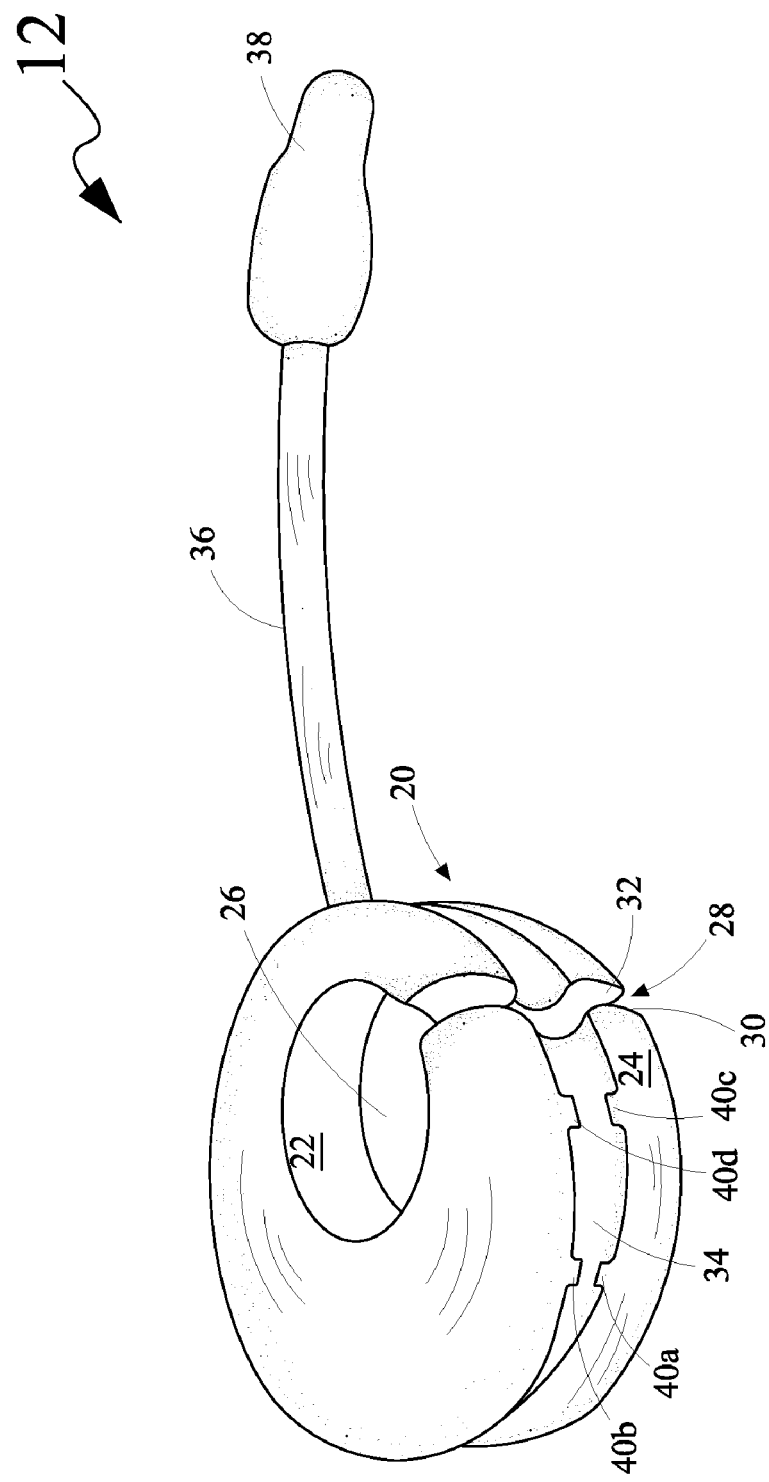
FIG. 2 illustrates a perspective view of a body member of the urinary catheter immobilizer of FIG. 1.

FIG. 2 illustrates a perspective view of the body member 12 of the urinary catheter immobilizer 100. The body member 12 is received over the second end portion 16 of the funnel-shaped member 10. The body member 12 includes a torus-shaped structure 20. The torus-shaped structure 20 includes an inner circumferential surface 22 and an outer circumferential surface 24. The inner circumferential surface 22 configures a cavity 26 capable of receiving an external portion of a urinary catheter (shown in FIG. 3) extending from a urinary meatus of a patient and the second end portion 16 of the funnel-shaped member 10. The torus-shaped structure 20 includes a vertical slit 28 configuring a first sidewall 30 and a second sidewall 32. The outer circumferential surface 24 includes at least one channel, such as a channel 34 running throughout a circumference of the torus-shaped structure 20 from the first sidewall 30 to the second sidewall 32. Further, the body member 12 includes an at least one elongated tubular structure, such as a tubular structure 36. More specifically, the at least one elongated tubular structure such as the tubular structure 36 extends from the outer circumferential surface 24 of the torus-shaped structure 20. The tubular structure 36 may also include a gripping element 38 for facilitating working of the tubular structure 36. The channel 34 on the outer circumferential surface 24 of the torus-shaped structure 20 is adapted to receive the tubular structure 36 when the tubular structure 36 is looped around the torus-shaped structure 20. The tubular structure 36 is capable of looping around the torus-shaped structure 20 for securing the body member 12 onto the external portion of the urinary catheter. The channel 34 may include plurality of protuberant portions such as protuberant portions 40a, 40b, 40c, and 40d hereinafter collectively referred to as protuberant portion 40. The protuberant portion 40 is capable of securely holding the tubular structure 36 within the channel 34.

Figure 3:
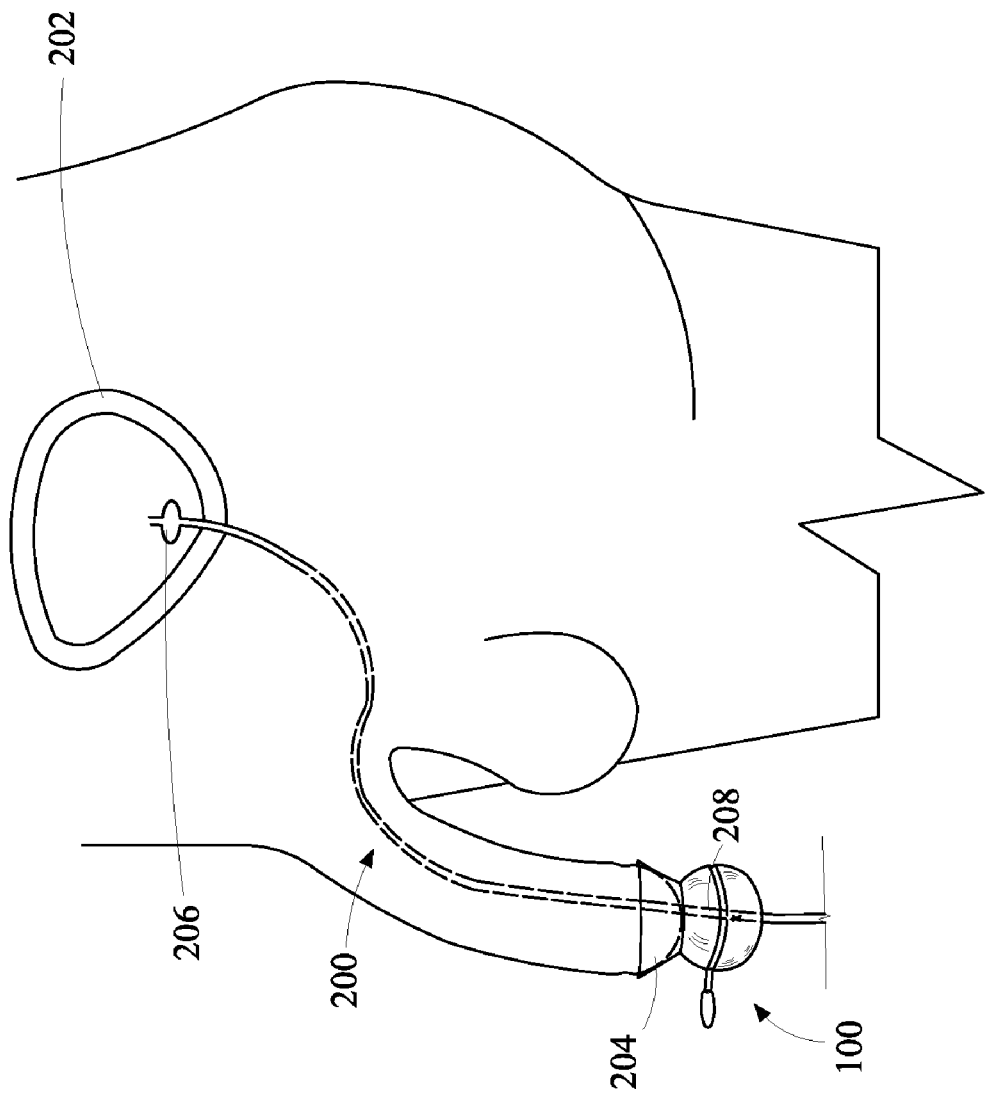
FIG. 3 illustrates securing of the urinary catheter immobilizer of FIG. 1 to a urinary meatus of a male patient, in accordance with an exemplary embodiment of the present invention.

FIG. 3 illustrates securing of the urinary catheter immobilizer 100 to a urinary meatus of a male patient, in accordance with an exemplary embodiment of the present invention. A urinary catheter such as a urinary catheter 200 is a hollow, flexible tube employed to drain urine from a urinary bladder 202 of a patient. The urinary catheter 200 is inserted through a urinary meatus 204 of the male patient to reach the urinary bladder 202, as such, a first end 206 of the urinary catheter 200 is receivable in the urinary bladder 202 and a second end (not shown) of the urinary catheter 200 remains outside the urinary meatus 204 which may be removably attached to a urine collection bag (not shown) for collecting urine. In male patients, the urinary catheter 200 is inserted into urinary tract through male genitals such as the urinary meatus 204. Upon insertion, the urinary catheter 200 may be immobilized with the help of the urinary catheter immobilizer 100, outside the human body. More specifically, the funnel-shaped member 10 and the body member 12 are made integral in a manner such that the oblong slit 18 of the funnel-shaped member 10 is in alignment with the vertical slit 28 of the body member 12 when the second end portion 16 of the funnel-shaped member 10 is received in the cavity 26 of the body member 12. The oblong slit 18 of the funnel-shaped member 10 and the vertical slit 28 of the body member 12 aligned in a same plane are capable of receiving an external portion 208 of the urinary catheter 200 proximate to the urinary meatus 204. The external portion 208 of the urinary catheter 200 proximate to the urinary meatus 204 is slid through the oblong slit 18 of the funnel-shaped member 10 and the vertical slit 28 of the body member 12 into a space configured by an inner portion (not shown) of the funnel-shaped member 10 and the cavity 26 of the body member 12.

After the external portion 208 of the urinary catheter 200 has been received in the space configured by the inner portion of the funnel-shaped member 10 and the cavity 26 of the body member 12, the funnel-shaped member 10 is received over the urinary meatus 204. More specifically, the first end portion 14 of the funnel-shaped member 10 is received over the urinary meatus 204. Further, the body member 12 is received on the external portion 208 of the urinary catheter 200 proximate to the urinary meatus 204. Thereafter, the at least one elongated tubular structure such as the tubular structure 36 is looped around the body member 12 for narrowing the cavity 26 in order to secure the urinary catheter 200. More specifically, the at least one channel such as the channel 34 of the torus-shaped structure 20 of the body member 12 receives the tubular structure 36 in a manner such that the tubular structure 36 is looped around the body member 12. The plurality of protuberant portions such as the protuberant portion 40 helps to keep the tubular structure 36 within the channel 34 in order to secure the body member 12 on the external portion 208 of the urinary catheter 200. The urinary catheter immobilizer 100 is capable of immobilizing movement of the urinary catheter 200 in and out of the urinary meatus 204. The attachment of the urinary catheter immobilizer 100 to the urinary catheter 200 minimizes the movement of the urinary catheter 200 within the urinary tract of the male patient and as such greatly reduces the chances of contracting the urinary tract infection caused by sliding of the urinary catheter 200 in and out of the human body through the urinary meatus 204.

Figure 4:
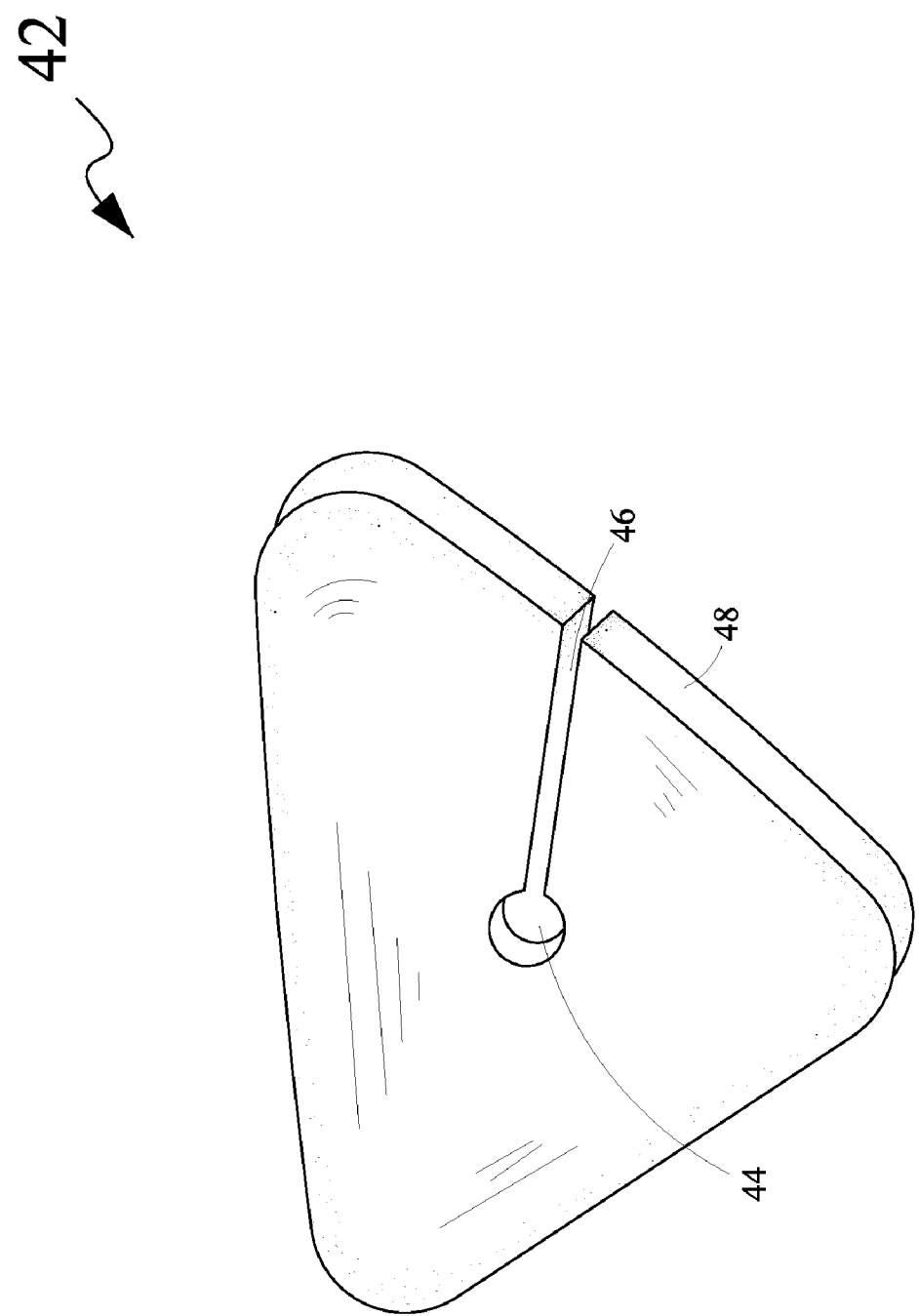
FIG. 4 illustrates a perspective view of an adapter pad, in accordance with an embodiment of the present invention.

Further, in order to accommodate differences in female anatomy, the urinary catheter immobilizer 100 includes an adapter pad 42 for female patients as shown in FIG. 4. The adapter pad 42 is an elastic triangular structure with a hole 44 configured in the center of the adapter pad 42. Further, a slit 46 is provided extending from the hole 44 to an edge portion 48 of the adapter pad 42. The hole 44 is configured to receive the urinary catheter 200. The adapter pad 42 is configured to be received over a urinary meatus of the female human body. The first end portion 14 of the funnel-shaped member 10 is configured to be received over the adapter pad 42. The body member 12 is configured to be received over the second end portion 16 of the funnel-shaped member 10. Thereafter, the body member 12 is capable of removably attaching to an external portion of the urinary catheter proximate to the urinary meatus of the female human body.

Figure 5:
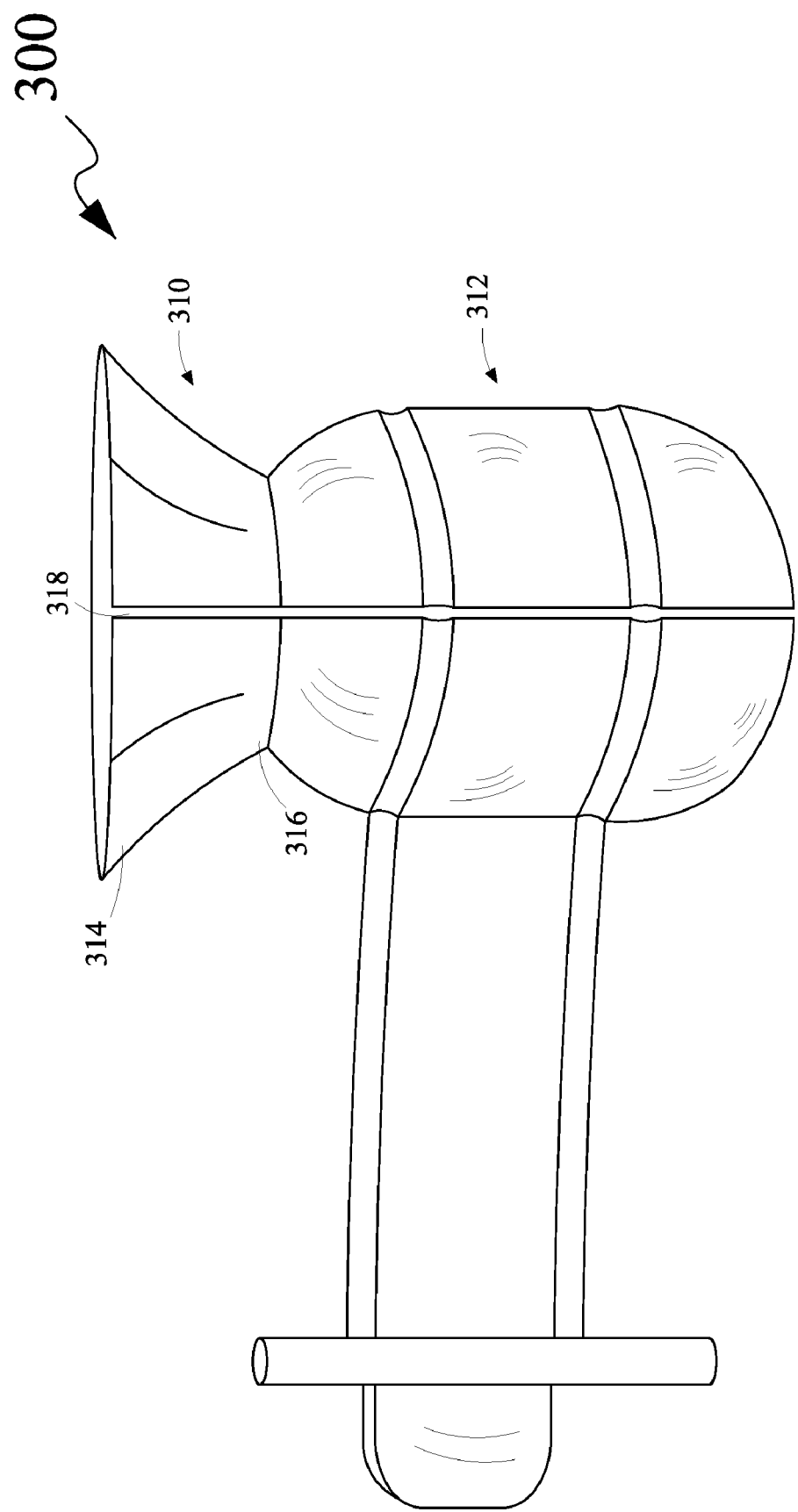
FIG. 5 illustrates a perspective view of a urinary catheter immobilizer, in accordance with another exemplary embodiment of the present invention.

The urinary catheter immobilizer 100 may be of multitude of size and shapes. FIG. 5 illustrates a urinary catheter immobilizer 300, such as the urinary catheter immobilizer 100 for immobilizing a urinary catheter (not shown), in accordance with another exemplary embodiment of the present invention. The urinary catheter immobilizer 300, as shown in FIG. 5, comprises a funnel-shaped member 310 and a body member 312 configured to be received over the funnel-shaped member 310. The funnel-shaped member 310 includes a first end portion 314 and a second end portion 316. The second end portion 316 is smaller in diameter than the first end portion 314. Further, an oblong slit 318 extends throughout the length of the funnel-shaped member 310, from the first end portion 314 to the second end portion 316. The funnel-shaped member 310 is similar in configuration to the funnel-shaped member 10 explained in conjunction with FIG. 1. The body member 312 is explained in detail in conjunction with FIG. 6.

Figure 6:
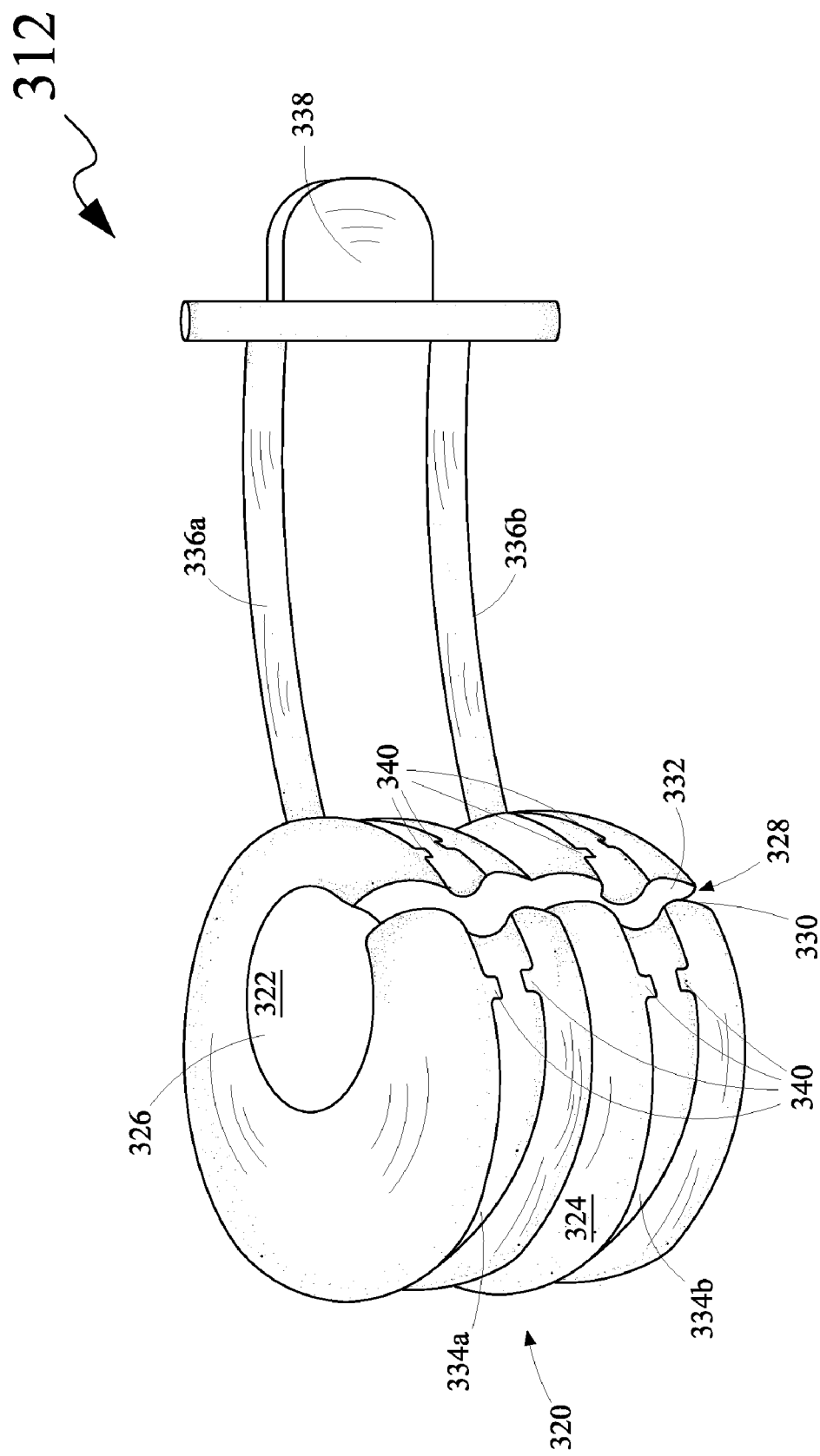
FIG. 6 illustrates a perspective view of a body member of the urinary catheter immobilizer of FIG. 5.

FIG. 6 illustrates a perspective view of the body member 312 of the urinary catheter immobilizer 300. The body member 312 includes a torus-shaped structure 320. The torus-shaped structure 320 has an inner circumferential surface 322 and an outer circumferential surface 324. The inner circumferential surface 322 configures a cavity 326 capable of receiving an external portion of a urinary catheter (not shown). The torus-shaped structure 320 includes a vertical slit 328 configuring a first sidewall 330 and a second sidewall 332. The outer circumferential surface 324 includes a plurality of channels such as channels 334a and 334b, extending throughout a circumference of the torus-shaped structure 320 from the first sidewall 330 to the second sidewall 332. Further, the body member 312 includes a plurality of elongated tubular structure such as tubular structures 336a and 336b, extending from the outer circumferential surface 324 of the torus-shaped structure 320. The plurality of elongated tubular structures is capable of being stretched to loop around the torus-shaped structure 320 and received within the plurality of channels such as the channels 334a and 334b. More specifically, the channels 334a and 334b on the outer circumferential surface 324 of the torus-shaped structure 320 is adapted to receive the tubular structures 336a and 336b respectively, when the tubular structures 336a and 336b are looped around the torus-shaped structure 320. The tubular structures 336a and 336b may have a gripping element such as a gripping element 338 that adjoins the tubular structures 336a and 336b and permits looping of the tubular structures 336a and 336b around the torus-shaped structure 320. Further, the plurality of channels such as the channels 334a and 334b may include plurality of protuberant portions such as protuberant portion 340. The protuberant portion 340 is capable of securing the tubular structures 336a and 336b within the channels 334a and 334b.

The best mode for carrying out the present invention is presented in terms of its preferred embodiment, herein illustrated with reference to FIGS. 1 to 6. However, the present invention is not limited to the described embodiment and a person skilled in the art will appreciate that many other embodiments of the present invention in terms of the configurations and functional features are possible without deviating from the scope of present invention and any such work will also fall under scope of the present invention.

The urinary catheter immobilizer such as the urinary catheter immobilizer 100, 300, as described herein, is compact, lightweight, user friendly and made of medically acknowledged safe materials. The material of construction of the urinary catheter immobilizer may include soft, elastic, medically tested material such as a silicone. It will be obvious to those skilled in the art that other materials which have been medically recognized to be safe may also be used for the construction of the urinary catheter immobilizer. In one embodiment of the present invention, the urinary catheter immobilizer may have a length of about 5 centimeters, a width of about 2 centimeters, and a diameter of the cavity of the body member may be around 0.5 centimeters.

A urinary catheter immobilizer, such as the urinary catheter immobilizer 100, 300, as described herein, offers the following advantages. The urinary catheter immobilizer is capable of being utilized for immobilizing movement of a urinary catheter. The urinary catheter immobilizer is capable of being used by male patients as well as female patients. The urinary catheter immobilizer is capable of being removably attached at any point along length of the external portion of the urinary catheter and precludes the need for inserting the urinary catheter into the immobilizer by an end point of the urinary catheter and as such the attachment and removal of the urinary catheter immobilizer is easy and user friendly. Further, the attachment of the urinary catheter immobilize to the urinary catheter minimizes the movement of the urinary catheter within the urinary tract of a patient and as such greatly reduces the chances of contracting urinary tract infection caused by sliding of the urinary catheter in and out of the human body through the urinary meatus.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, to thereby enable others skilled in the art to best utilize the present invention and various embodiments with various modifications as are suited to the particular use contemplated. It is understood that various omission and substitutions of equivalents are contemplated as circumstance may suggest or render expedient, but such are intended to cover the application or implementation without departing from the spirit or scope of the claims of the present invention

What is claimed is:

1. A urinary catheter immobilizer for immobilizing movement of a urinary catheter in a human body, the urinary catheter immobilizer comprising:
    a funnel-shaped member having a first end portion and a second end portion, wherein the first end portion is capable of being received over a urinary meatus of a human body, the funnel-shaped member comprising an oblong slit extending from the first end portion to the second end portion; and
    a body member of the immobilizer configured to be received over the second end portion of the funnel-shaped member of the immobilizer, the body member of the immobilizer capable of removably attaching to an external portion of the urinary catheter proximate to the urinary meatus of the human body, the body member of the immobilizer comprising,
        a torus-shaped structure having an inner circumferential surface and an outer circumferential surface, the torus-shaped structure comprising a slit configuring a first sidewall and a second sidewall, the inner circumferential surface configuring a cavity for receiving the external portion of the urinary catheter and the outer circumferential surface comprising at least one channel, and
        at least one elongated tubular structure extending from the outer circumferential surface of the torus-shaped structure, the at least one elongated tubular structure adapted to be received in the at least one channel for looping around the torus-shaped structure for securing the body member of the immobilizer onto the external portion of the urinary catheter.

2. The urinary catheter immobilizer of claim 1, wherein the funnel-shaped member is made of silicone.

3. The urinary catheter immobilizer of claim 1, wherein the body member of the immobilizer is made of silicone.

4. A urinary catheter immobilizer for immobilizing movement of a urinary catheter in a female human body, the urinary catheter immobilizer comprising:
    an adapter pad comprising a hole for receiving the external portion of the urinary catheter and a slit extending from the hole to an edge portion of the adapter pad, the adapter pad configured to be received over a urinary meatus of the female human body;
    a funnel-shaped member having a first end portion and a second end portion, and an oblong slit extending from the first end portion to the second end portion wherein the first end portion is configured to be received over the adapter pad; and
    a body member of the immobilizer configured to be received over the second end portion of the funnel-shaped member, the body member of the immobilizer capable of removably attaching to an external portion of the urinary catheter proximate to the urinary meatus of the female human body, the body member of the immobilizer comprising,
        a torus-shaped structure having an inner circumferential surface and an outer circumferential surface, the torus-shaped structure comprising a slit configuring a first sidewall and a second sidewall, the inner circumferential surface configuring a cavity for receiving the external portion of the urinary catheter and the outer circumferential surface comprising at least one channel, and
        at least one elongated tubular structure extending from the outer circumferential surface of the torus-shaped structure, the at least one elongated tubular structure adapted to be received in the at least one channel for looping around the torus-shaped structure for securing the body member of the immobilizer onto the external portion of the urinary catheter.

5. The urinary catheter immobilizer of claim 4, wherein the funnel-shaped member is made of silicone.

6. The urinary catheter immobilizer of claim 4, wherein the body member of the immobilizer is made of silicone.

* * * * *